(12) United States Patent
Dohi et al.

(10) Patent No.: US 9,340,740 B2
(45) Date of Patent: *May 17, 2016

(54) METHOD FOR EVALUATING THERMAL PLASTICITY OF COALS AND CAKING ADDITIVES, AND METHOD FOR PRODUCING COKE

(75) Inventors: Yusuke Dohi, Hiroshima (JP); Izumi Shimoyama, Okayama (JP); Kiyoshi Fukada, Hiroshima (JP); Tetsuya Yamamoto, Hiroshima (JP); Hiroyuki Sumi, Kanagawa (JP)

(73) Assignee: JFE STEEL CORPORATION, Tokyo (JP)

( * ) Notice: Subject to any disclaimer, the term of this patent is extended or adjusted under 35 U.S.C. 154(b) by 565 days.

This patent is subject to a terminal disclaimer.

(21) Appl. No.: 13/820,292

(22) PCT Filed: Aug. 31, 2011

(86) PCT No.: PCT/JP2011/070316
§ 371 (c)(1),
(2), (4) Date: Jun. 6, 2013

(87) PCT Pub. No.: WO2012/029985
PCT Pub. Date: Mar. 8, 2012

(65) Prior Publication Data
US 2014/0144071 A1    May 29, 2014

(30) Foreign Application Priority Data
Sep. 1, 2010   (JP) .................................. 2010-195622
Sep. 1, 2010   (WO) .................. PCT/JP2010/065351

(51) Int. Cl.
*G01N 3/54* (2006.01)
*C10L 5/28* (2006.01)
(Continued)

(52) U.S. Cl.
CPC . *C10L 5/28* (2013.01); *C10B 45/00* (2013.01); *C10B 57/06* (2013.01); *G01N 3/54* (2013.01); *G01N 11/00* (2013.01); *G01N 13/04* (2013.01); *G01N 33/222* (2013.01)

(58) Field of Classification Search
CPC .............................. G01N 33/222; G01N 3/54
USPC ................................... 44/607, 903; 73/78–85
See application file for complete search history.

(56) References Cited

U.S. PATENT DOCUMENTS 4,074,561 A * 2/1978 Brockschmidt et al. ........ 374/23
5,207,507 A * 5/1993 Kimoto et al. .................. 374/14
(Continued)

FOREIGN PATENT DOCUMENTS

| JP | 10-148632 | 6/1998 |
| JP | 2010-190761 | 9/2010 |

OTHER PUBLICATIONS

Extended European Search Report dated Apr. 2, 2014; Application No. 14160526.1.
(Continued)

*Primary Examiner* — Ellen McAvoy
(74) *Attorney, Agent, or Firm* — Young & Thompson

(57) ABSTRACT

A method for evaluating thermal plasticity of coals and caking additives includes packing a coal or a caking additive into a vessel to prepare a sample 1; arranging a through-hole material 2 having through-holes from top to bottom surfaces, onto the sample 1; heating the sample 1 at a predetermined heating rate while maintaining a constant volume of or while applying a constant load onto the sample 1 and the through-hole material 2; measuring the permeation distance with which the molten sample has permeated into the through-holes; and evaluating thermal plasticity of the sample using the measured value. Alternatively, a method involves heating the sample 1 at a predetermined heating rate while maintaining the sample 1 and the through-hole material 2 in a constant volume; measuring the pressure of the sample that is transmitted via the through-hole material 2; and evaluating thermal plasticity of the sample using the measured value.

25 Claims, 6 Drawing Sheets

(51) Int. Cl.
*C10B 45/00* (2006.01)
*C10B 57/06* (2006.01)
*G01N 11/00* (2006.01)
*G01N 13/04* (2006.01)
*G01N 33/22* (2006.01)

(56) References Cited

U.S. PATENT DOCUMENTS

| | | | | |
|---|---|---|---|---|
| 5,366,901 | A * | 11/1994 | Bergli et al. | 436/133 |
| 5,952,561 | A * | 9/1999 | Jaselskis et al. | 73/78 |
| 7,799,100 | B2 * | 9/2010 | Harada et al. | 44/282 |
| 7,901,473 | B2 * | 3/2011 | Weinberg et al. | 44/620 |
| 8,272,247 | B2 * | 9/2012 | Kojovic et al. | 73/12.11 |
| 2013/0255142 | A1 * | 10/2013 | Dohi et al. | 44/550 |

OTHER PUBLICATIONS

Extended European Search Report dated Mar. 5, 2014; Application No. 11821995.5.
Koichi Matsuoka et al., "Apparent Coal Viscosity Estimated from Needle Penetration into Pellet of Pulverized Coal Particles", ISIJ International, vol. 36, No. 1, 1996, pp. 40-44, XP055093088.
International Search Report PCT/JP2011/070316 dated Dec. 6, 2011.
Kentaro Iwamoto et al., "Kaatsu Ryudosho Nensho de Seisei suru Sekitanbai ni Kansuru Kenkyu", The Japan Institute of Energy Taikai Koen Yoshishu, Jul. 31, 2001, vol. 10th, pp. 148 to 151.
Hiroyuki Sumi et al., "Effect of Bubble Growth on Coarse Defect Generation Behavior in Coke", Journal of the Iron & Steel Institute of Japan, Jun. 4, 2010, vol. 96, No. 5, pp. 258 to 264.

* cited by examiner

METHOD FOR EVALUATING THERMAL PLASTICITY OF COALS AND CAKING ADDITIVES, AND METHOD FOR PRODUCING COKE

TECHNICAL FIELD

The present invention relates to a method for evaluating thermal plasticity of coals and caking additives during carbonization. The method is one of the approaches for evaluating the quality of coking coals and caking additives. The invention also relates to a method for producing coke using the evaluation method.

BACKGROUND ART

In a blast furnace method which is the most common method for pig iron production, coke plays a number of roles, for example as a reducing agent for iron ore, as a heat source and as a spacer. In order to operate a blast furnace stably and efficiently, it is important that the gas permeability in the blast furnace be maintained. Thus, there has been a need for high-strength coke to be produced. Coke is produced by carbonization of a coal blend, which is a blend of various types of coking coals that have been crushed, in a coke oven. During carbonization, coking coal softens and melts at temperatures in the range of about 300° C. to 550° C. and, at the same time, volatile matters are driven off to form a gas which causes swelling, whereby particles are adhered together to give a mass of semicoke. The semicoke is thereafter densified by being contracted in the course where the temperature is raised to near 1000° C., resulting in a rigid coke (a coke cake). Thus, the adhesiveness of thermally plastic coal greatly influences properties such as coke strength and particle diameter after carbonization.

In order to enhance the adhesion of coking coal (coal blend), a coke producing method is generally adopted in which a coal blend is mixed with a caking additive that exhibits high fluidity at temperatures where the coal becomes softened and molten. Here, examples of the caking additives include tar pitches, petroleum pitches, solvent-refined coals and solvent-extracted coals. Similarly to coal, the adhesiveness of these caking additives in a thermally plastic state greatly affects coke properties after carbonization.

In the production of coke in a coke oven, carbonized coke is discharged from the coke oven with a pushing machine. If the degree of shrinkage of the produced coke cake itself is low, discharging out of the oven becomes difficult. This can lead to a "stickers (or hard push)", namely, a problem in which the coke cannot be discharged from the oven. The structure of a carbonized coke cake is largely affected by volume changes of coal and semicoke during the carbonization process. It is known that the shrinkage of semicoke has a good correlation with the volatile content of coal (see, for example, Non Patent Literature 1). In many cases, the volatile contents of coal blends are controlled to be substantially constant for operations in the same plant. Thus, volume-change characteristics of plastic coal greatly affect the structure of a carbonized coke cake.

As mentioned above, thermal plasticity of coal is very important due to their great influences on coke properties and coke cake structures after carbonization. Thus, methods for measuring these characteristics have been studied actively since old times. In particular, coke strength, which is an important coke quality, is largely affected by properties of raw-material coal, especially coal rank and thermal plasticity. Thermal plasticity is exhibited when coal becomes softened and molten when heated, and are usually measured and evaluated with respect to properties such as fluidity, viscosity, adhesiveness and swellability of thermally plastic coal.

Of the thermal plasticity of coal, the fluidity of thermally plastic coal is commonly measured by a coal fluidity testing method based on a Gieseler plastometer method specified in JIS M 8801. According to a Gieseler plastometer method, coal that has been crushed to sizes of not more than 425 µm is placed in a prescribed crucible and is heated at a specified temperature increase rate while the rotational speed of a stirring rod under a specified torque is read on a dial and is indicated in terms of ddpm (dial division per minute).

While a Gieseler plastometer method measures the rotational speed of a stirring rod under a constant torque, other methods evaluate the torque at a constant rotational speed. For example, Patent Literature 1 describes a method in which the torque is measured while rotating a rotor at a constant rotational speed.

Aimed at measuring viscosity that is a physically significant thermal plasticity, there are methods for measuring viscosity with a dynamic viscoelastometer (see, for example, Patent Literature 2). Dynamic viscoelastometry is a measurement of viscoelastic behaviors observed when a viscoelastic body is subjected to periodic forces. In the method described in Patent Literature 2, the viscosity of thermally plastic coal is evaluated based on complex viscosity coefficient among parameters obtained by the measurement. This method is characterized in that the viscosity of thermally plastic coal is measurable at a given shear rate.

Further, it has been reported that thermal plasticity of coal is evaluated by measuring the adhesion of thermally plastic coal with respect to activated carbon or glass beads. In such a method, a small amount of a coal sample, sandwiched vertically between activated carbons or glass beads, is heated to thermal plasticity and is thereafter cooled, and the adhesion of the coal with respect to the activated carbons or the glass beads is visually observed.

A common method for measuring the swellability of thermally plastic coal is a dilatometer method specified in JIS M 8801. In a dilatometer method, coal that has been crushed to sizes of not more than 250 µm is compacted by a specified method, placed into a prescribed crucible and heated at a specified temperature increase rate while the displacement of the coal is measured over time using a detection rod arranged on the top of the coal.

In order to simulate thermally plastic behaviors of coal in a coke oven, coal swellability testing methods are known which achieve enhanced simulation of permeation behaviors for a gas generated during the plasticization of coal (see, for example, Patent Literature 3). According to such a method, a permeable material is arranged between a coal layer and a piston or is arranged between a coal layer and a piston as well as at the bottom of the coal layer so as to increase pathways through which volatile matters and liquid substances generated from the coal can pass, thereby approximating the measurement environment more closely to an environment in which swelling behaviors actually occur in a coke oven. A similar method is also known in which the swellability of coal is measured by arranging a material having a through pathway onto a coal layer and microwave-heating the coal while applying a load thereto (see Patent Literature 4).

CITATION LIST

Patent Literature

[PTL 1] Japanese Unexamined Patent Application Publication No. 6-347392

[PTL 2] Japanese Unexamined Patent Application Publication No. 2000-304674
[PTL 3] Japanese Patent No. 2855728
[PTL 4] Japanese Unexamined Patent Application Publication No. 2009-204609

Non Patent Literature

[NPL 1] C. Meyer et al.: "Gluckauf Forshungshefte", Vol. 42, 1981, pp. 233-239
[NPL 2] Morotomi et al.: "Journal of the Fuel Society of Japan", Vol. 53, 1974, pp. 779-790
[NPL 3] D. W. van Krevelen: "Coal", 1993, pp. 693-695
[NPL 4] Miyazu et al.: "Nippon Kokan Gihou (Nippon Kokan Technical Report)", Vol. 67, 1975, pp. 125-137
[NPL 5] Kamioka et al.: "Tetsu to Hagane (Iron and Steel)", Vol. 93, 2007, pp. 728-735

Technical Problem

In order to evaluate thermally plastic behaviors of coal in a coke oven, it is necessary that thermal plasticity of coal be measured while simulating the environment that will surround the thermally plastic coal in a coke oven. Coal plasticized in a coke oven, as well as an environment surrounding the coal will be described in detail below.

In a coke oven, thermally plastic coal is constrained between adjacent layers. Because the thermal conductivity of coal is low, coal in a coke oven is not heated uniformly and presents different states. That is, it forms a coke layer, a thermally plastic layer and a coal layer from the oven wall side, namely, the heating face side. Although the coke oven itself is slightly swollen during carbonization, there is substantially no deformation. Thus, the thermally plastic coal is constrained between the adjacent coke layer and coal layer.

Further, thermally plastic coal is surrounded by a large number of defective structures such as voids between coal particles in a coal layer, interparticle voids in the thermally plastic coal, large pores formed by the volatilization of thermally decomposed gas, and cracks in an adjacent coke layer. In particular, cracks that have occurred in a coke layer are considered to be about several hundreds of micrometers to several millimeters in width, larger than inter coal particle voids or pores whose sizes are about several tens to several hundreds of micrometers. Thus, it is probable that not only thermally decomposed gases and liquid substances which are byproducts from coal, but also thermally plastic coal itself will permeate into such large defects formed in a coke layer. Further, the shear rate acting on thermally plastic coal during permeation is expected to be different from brand to brand.

As mentioned above, constraint conditions and permeation conditions need to be optimized in order to measure thermal plasticity of coal while simulating the environment that will surround the thermally plastic coal in a coke oven. However, existing methods have the following problems.

In a Gieseler plastometer method, measurement is carried out with respect to coal placed in a vessel. Thus, this method has a problem in that no considerations are given to constraint conditions or permeation conditions. Further, this method is not suited for the measurement of coal that exhibits high fluidity. The reason is because when highly fluid coal is measured, a phenomenon occurs in which the vicinity of the inner wall of a vessel becomes empty (Weissenberg effect) and a stirring rod is rotated at idle and can fail to evaluate fluidity accurately (see, for example, Non Patent Literature 2).

Similarly, methods based on torque measurement at a constant revolution speed are problematic in that constraint conditions and permeation conditions are not considered. Further, because the measurement is performed at a constant shear rate, such methods cannot compare and evaluate thermal plasticity of coals accurately for the reason described above.

A dynamic viscoelastometer is an apparatus dedicated to measuring viscosity as a thermal plasticity and capable of viscosity measurement at any shear rate. Thus, the viscosity of thermally plastic coal in a coke oven is measurable by setting the shear rate in the measurement to a value of shearing that will act on the coal in a coke oven. However, it is usually difficult to measure beforehand or estimate the rate of shearing in a coke oven for each brand.

Reproduction of permeation conditions in terms of the presence of a coal layer is attempted in methods which evaluate thermal plasticity of coal by measuring the adhesion with respect to activated carbon or glass beads. However, such methods have a problem in that they do not simulate the presence of a coke layer and large defects, as well as in that the measurement is not constraint.

The coal swellability testing method of Patent Literature 3 which involves the use of a permeable material considers the movement of gases and liquid substances generated from coal. However, this method is problematic in that the movement of thermally plastic coal itself is not addressed. The reason for this neglect is because the permeability of the permeable material used in Patent Literature 3 is not high enough for thermally plastic coal to permeate the material. The present inventors actually carried out a test according to the description in Patent Literature 3 to confirm that thermally plastic coal did not permeate the permeable material. Accordingly, it is necessary that new conditions be designed to allow thermally plastic coal to permeate the permeable material.

Patent Literature 4 discloses a similar method for measuring swellability of coal by arranging a material having a through pathway onto a coal layer, in consideration for the movements of gases and liquid substances generated from the coal. However, this method has problems in that the heating method is limited and in that the literature does not specify conditions for evaluating a permeation phenomenon in a coke oven. Further, Patent Literature 4 does not clearly describe a relationship between a permeation phenomenon and a thermally plastic behavior of coal melt, and does not indicate a relationship between the permeation phenomenon of coal melt and the quality of produced coke. Thus, this literature does not address the production of high-quality coke.

As described above, the existing techniques are incapable of measuring thermal plasticity of coals and caking additives such as fluidity, viscosity, adhesiveness, permeation properties, swelling coefficient during permeation, and pressure during permeation, while sufficiently simulating the environment that will surround thermally plastic coals and caking additives in a coke oven.

In order to solve the aforementioned problems in the art and to realize the measurement of thermal plasticity of coals and caking additives while sufficiently simulating the environment that will surround thermally plastic coals and caking additives in a coke oven, it is an object of the present invention to provide a simple and more accurate method for evaluating thermal plasticity of coals and caking additives.

Further, higher accuracy in the evaluation of thermal plasticity makes it possible to understand the influences of coals and caking additives on coke strength more accurately. By utilizing these findings, another object of the invention is to provide a method for producing high-strength coke by setting a new criterion for the blending of coals.

Solution to Problem

Characteristics of the present invention aimed at solving the aforementioned problems are summarized as follows.

(1) A method for evaluating thermal plasticity of coals and caking additives, including:
packing a coal or a caking additive into a vessel to prepare a sample,
arranging a material having through-holes from top to bottom surfaces, onto the sample,
heating the sample while maintaining the sample and the through-hole material in a constant volume,
measuring the permeation distance with which the molten sample has permeated into the through-holes, and
evaluating thermal plasticity of the sample using the measured value.

(2) A method for evaluating thermal plasticity of coals and caking additives, including:
packing a coal or a caking additive into a vessel to prepare a sample,
arranging a through-hole material having through-holes from top to bottom surfaces, onto the sample,
heating the sample while maintaining the sample and the through-hole material in a constant volume,
measuring the pressure of the sample that is transmitted via the through-hole material, and
evaluating thermal plasticity of the sample using the measured value.

(3) A method for evaluating thermal plasticity of coals and caking additives, including:
packing a coal or a caking additive into a vessel to prepare a sample,
arranging a through-hole material having through-holes from top to bottom surfaces, onto the sample,
heating the sample while applying a constant load onto the through-hole material,
measuring the permeation distance with which the molten sample has permeated into the through-holes, and
evaluating thermal plasticity of the sample using the measured value.

(4) A method for evaluating thermal plasticity of coals and caking additives, including:
packing a coal or a caking additive into a vessel to prepare a sample,
arranging a through-hole material having through-holes from top to bottom surfaces, onto the sample,
heating the sample while applying a constant load onto the through-hole material,
measuring the swelling coefficient of the sample, and
evaluating thermal plasticity of the sample using the measured value.

(5) The method for evaluating thermal plasticity of coals and caking additives described in any of (1) to (4), wherein the preparation of the sample includes crushing a coal or a caking additive such that particles with a particle diameter of not more than 3 mm account for not less than 70 mass %, and packing the crushed coal or caking additive into a vessel with a packing density of 0.7 to 0.9 g/cm$^3$ and a layer thickness of 5 to 20 mm.

(6) The method for evaluating thermal plasticity of coals and caking additives described in (5), wherein the coal or the caking additive is crushed such that particles with a particle diameter of not more than 2 mm account for 100 mass %.

(7) The method for evaluating thermal plasticity of coals and caking additives described in any of (1) to (4), wherein the through-hole material is a spherical particle-packed layer or a non-spherical particle-packed layer.

(8) The method for evaluating thermal plasticity of coals and caking additives described in (7), wherein the through-hole material is a spherical particle-packed layer.

(9) The method for evaluating thermal plasticity of coals and caking additives described in (8), wherein the spherical particle-packed layer include glass beads.

(10) The method for evaluating thermal plasticity of coals and caking additives described in any of (1) to (4), wherein the sample is heated from room temperature to 550° C. at a heating rate of 2 to 10° C./min in an inert gas atmosphere.

(11) The method for evaluating thermal plasticity of coals and caking additives described in (10), wherein the heating rate is 2 to 4° C./min.

(12) The method for evaluating thermal plasticity of coals and caking additives described in (3) or (4), wherein the application of a constant load includes applying such a load that the pressure to the top surface of the through-hole material becomes 5 to 80 kPa.

(13) The method for evaluating thermal plasticity of coals and caking additives described in (12), wherein the application of a load includes applying such a load that the pressure to the top surface of the through-hole material becomes 15 to 55 kPa.

(14) The method for evaluating thermal plasticity of coals and caking additives described in (1) or (2), wherein
arranging of the through-hole material includes arranging glass beads having a diameter of 0.2 to 3.5 mm onto the sample so as to obtain a layer thickness of 20 to 100 mm, and
heating of the sample includes heating the sample from room temperature to 550° C. at a heating rate of 2 to 10° C./min in an inert gas atmosphere while maintaining the sample and the glass bead layer in a constant volume.

(15) The method for evaluating thermal plasticity of coals and caking additives described in (3) or (4), wherein
arranging of the through-hole material includes arranging glass beads having a diameter of 0.2 to 3.5 mm onto the sample so as to obtain a layer thickness of 20 to 100 mm, and
heating of the sample includes heating the sample from room temperature to 550° C. at a heating rate of 2 to 10° C./min in an inert gas atmosphere while applying a load from above the glass beads such that 5 to 80 kPa is obtained.

(16) The method for evaluating thermal plasticity of coals and caking additives described in (1) or (2), wherein
the preparation of the sample includes crushing a coal or a caking additive such that particles with a particle diameter of not more than 3 mm account for not less than 70 mass %, and packing the crushed coal or caking additive into a vessel with a packing density of 0.7 to 0.9 g/cm$^3$ and a layer thickness of 5 to 20 mm,
arranging of the through-hole material includes arranging glass beads having a diameter of 0.2 to 3.5 mm onto the sample so as to obtain a layer thickness of 20 to 100 mm, and
heating of the sample includes heating the sample from room temperature to 550° C. at a heating rate of 2 to 10° C./min in an inert gas atmosphere while maintaining the sample and the glass bead layer in a constant volume.

(17) The method for evaluating thermal plasticity of coals and caking additives described in (3) or (4), wherein
the preparation of the sample includes crushing a coal or a caking additive such that particles with a particle diameter of not more than 3 mm account for not less than 70 mass %, and packing the crushed coal or caking additive into a vessel with a packing density of 0.7 to 0.9 g/cm³ and a layer thickness of 5 to 20 mm, arranging of the through-hole material includes arranging glass beads having a diameter of 0.2 to 3.5 mm onto the sample so as to obtain a layer thickness of 20 to 100 mm, and heating of the sample includes heating the sample from room temperature to 550° C. at a heating rate of 2 to 10° C./min in an inert gas atmosphere while applying a load from above the glass beads such that 5 to 80 kPa is obtained.

(18) The method for evaluating thermal plasticity of coals and caking additives described in (1) or (2), wherein the preparation of the sample includes crushing a coal or a caking additive such that particles with a particle diameter of not more than 2 mm account for 100 mass %, and packing the crushed coal or caking additive into a vessel with a packing density of 0.8 g/cm³ and a layer thickness of 10 mm, arranging of the through-hole material includes arranging glass beads having a diameter of 2 mm onto the sample so as to obtain a layer thickness of 80 mm, and heating of the sample includes heating the sample from room temperature to 550° C. at a heating rate of 3° C./min in an inert gas atmosphere while maintaining the sample and the glass bead layer in a constant volume.

(19) The method for evaluating thermal plasticity of coals and caking additives described in (3) or (4), wherein the preparation of the sample includes crushing a coal or a caking additive such that particles with a particle diameter of not more than 2 mm account for 100 mass %, and packing the crushed coal or caking additive into a vessel with a packing density of 0.8 g/cm³ and a layer thickness of 10 mm, arranging of the through-hole material includes arranging glass beads having a diameter of 2 mm onto the sample so as to obtain a layer thickness of 80 mm, and heating of the sample includes heating the sample from room temperature to 550° C. at a heating rate of 3° C./min in an inert gas atmosphere while applying a load from above the glass beads such that 50 kPa is obtained.

(20) A method for producing coke, including:

measuring the permeation distance, which is a thermal plasticity of coal, with respect to a coal or coals to be added to a coking coal blend that have a logarithmic value of Gieseler maximum fluidity, log MF, of not less than 3.0, based on a weighted-average value of the measured permeation distance(s), determining the blend ratio of the coal(s) having a logarithmic value of Gieseler maximum fluidity, log MF, of not less than 3.0, and carbonizing coals that have been blended according to the determined blend ratio.

(21) The method for producing coke described in (20), wherein the permeation distance is measured by (1) to (4) below, and the blend ratio is determined by determining the proportion(s) of the coal(s) having a logarithmic value of Gieseler maximum fluidity, log MF, of not less than 3.0 such that the weighted-average value of the measured permeation distance(s) becomes not more than 15 mm, (1) a coal or a caking additive is crushed such that particles with a particle diameter of not more than 2 mm account for 100 mass %, and the crushed coal or caking additive is packed into a vessel with a packing density of 0.8 g/cm³ and a layer thickness of 10 mm, thereby preparing a sample, (2) glass beads having a diameter of 2 mm are arranged onto the sample so as to obtain a layer thickness of 80 mm, (3) the sample is heated from room temperature to 550° C. at a heating rate of 3° C./min in an inert gas atmosphere while maintaining the sample and the glass bead layer in a constant volume, (4) the permeation distance of the molten sample that has permeated into the glass bead layer is measured.

(22) The method for producing coke described in (20), wherein the permeation distance is measured by (1) to (4) below, and the blend ratio is determined by determining the proportion(s) of the coal(s) having a logarithmic value of Gieseler maximum fluidity, log MF, of not less than 3.0 such that the weighted-average value of the measured permeation distance(s) becomes not more than 17 mm, (1) a coal or a caking additive is crushed such that particles with a particle diameter of not more than 2 mm account for 100 mass %, and the crushed coal or caking additive is packed into a vessel with a packing density of 0.8 g/cm³ and a layer thickness of 10 mm, thereby preparing a sample, (2) glass beads having a diameter of 2 mm are arranged onto the sample so as to obtain a layer thickness of 80 mm, (3) the sample is heated from room temperature to 550° C. at a heating rate of 3° C./min in an inert gas atmosphere while applying a load from above the glass beads such that 50 kPa is obtained, (4) the permeation distance of the molten sample that has permeated into the glass bead layer is measured.

(23) A method for producing coke, including:

determining beforehand brands of coals or caking additives to be added to a coking coal blend, as well as the total blend ratio of a coal or coals with log MF of less than 3.0 relative to the coal blend, measuring the permeation distance with respect to a coal or coals having a logarithmic value of Gieseler maximum fluidity, log MF, of not less than 3.0, among the coals to be added to the coking coal blend, determining a relationship between the weighted-average permeation distance of the coals or caking additives with log MF of not less than 3.0 that are to be added to the coal blends, and the coke strength obtained with the coal blends prepared while changing the proportions of the individual brands of coals, the relationship being obtained by changing the proportions of the individual brands of coals or caking additives with the total blend ratio of the coal or coals with log MF of less than 3.0 being kept constant relative to the coal blend, and adjusting the weighted-average permeation distance by controlling the brand and the proportion of the coal(s) with log MF of not less than 3.0 so as to achieve coke strength that is not less than a desired value.

(24) The method for producing coke described in (23), wherein the permeation distance is measured under conditions selected from the range described below:

a coal or a caking additive is crushed such that particles with a particle diameter of not more than 3 mm account for not less than 70 mass %; the crushed material is packed into a vessel with a packing density of 0.7 to 0.9 g/cm³ and a layer thickness of 5 to 20 mm, thereby preparing a sample; glass beads having a diameter of 0.2 to 3.5 mm are arranged onto the sample so as to obtain a layer thickness of 20 to 100 mm; and the sample is heated from room temperature to 550° C. at a temperature increase rate of 2 to 10° C./min in an inert gas atmosphere while maintaining the sample and the glass bead layer in a constant volume.

(25) The method for producing coke described in (23), wherein the permeation distance is measured under conditions selected from the range described below:

a coal or a caking additive is crushed such that particles with a particle diameter of not more than 3 mm account for not less than 70 mass %; the crushed material is packed into a vessel with a packing density of 0.7 to 0.9 g/cm$^3$ and a layer thickness of 5 to 20 mm, thereby preparing a sample; glass beads having a diameter of 0.2 to 3.5 mm are arranged onto the sample so as to obtain a layer thickness of 20 to 100 mm; and the sample is heated from room temperature to 550° C. at a temperature increase rate of 2 to 10° C./min in an inert gas atmosphere while applying a load from above the glass beads such that a pressure of 5 to 80 kPa is obtained.

Advantageous Effects of Invention

According to the present invention, it is possible to evaluate thermal plasticity of coals and caking additives, namely, the permeation distance of a thermal plastic into defective structures, the swelling coefficient during permeation, and the pressure during permeation while simulating the influences of defective structures that will be present around the thermally plastic layer of coals and caking additives in a coke oven, in particular the influences of cracks present in a coke layer adjacent to the thermally plastic layer, as well as appropriately reproducing constraint conditions that will surround the thermal plastic in a coke oven. In detail, the invention makes it possible to measure the permeation distance of a thermal plastic into defective structures, the swelling coefficient during permeation, and the pressure during permeation while simulating a shear rate at which coals and caking additives that have been plasticized in a coke oven will move and change forms. With the measured values, coke properties and coke cake structures can be estimated with higher accuracy than achieved by conventional methods.

Thus, thermally plastic behaviors of coal in a coke oven can be evaluated accurately, and the obtained data can be utilized in the producing of high-strength coke.

DESCRIPTION OF EMBODIMENTS

Figure 1:
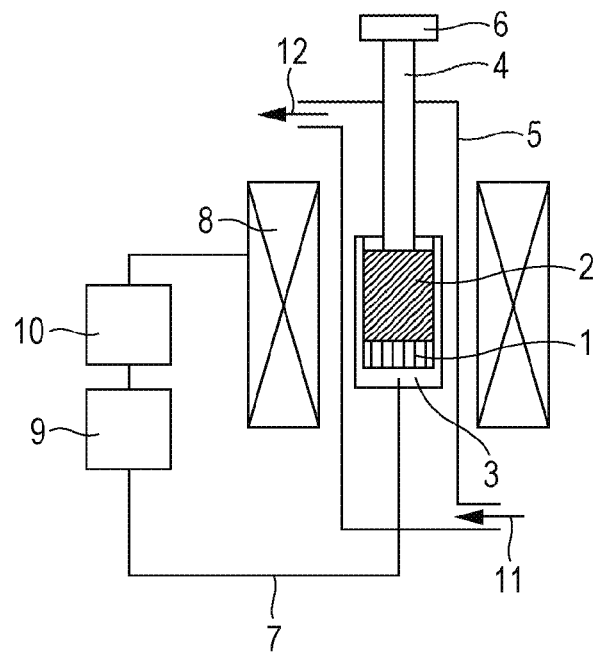
FIG. 1 is a schematic view illustrating an example of an apparatus for use in the invention for measuring thermal plasticity while maintaining a sample and a through-hole material having through-holes from top to bottom surfaces in a constant volume.
Figure 2:
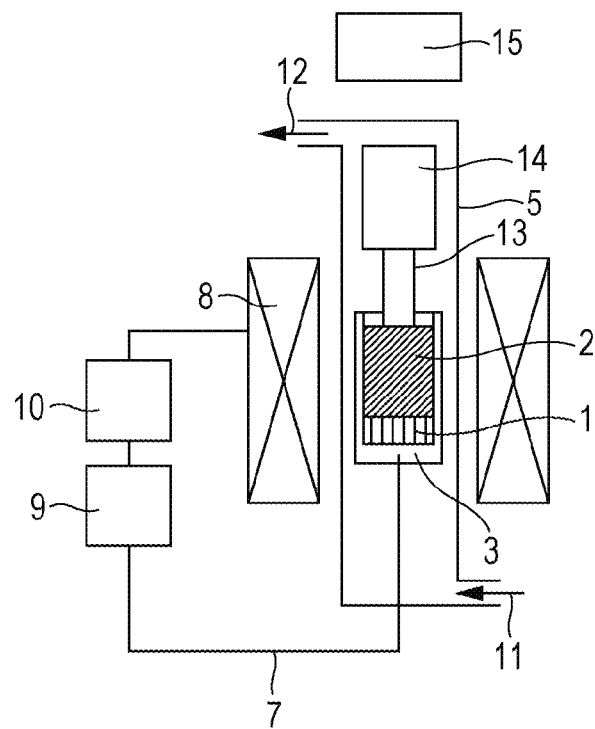
FIG. 2 is a schematic view illustrating an example of an apparatus for use in the invention for measuring thermal plasticity while applying a constant load onto a sample and a through-hole material.

Exemplary apparatuses used in the invention to measure thermal plasticity are illustrated in FIGS. 1 and 2. The apparatus illustrated in FIG. 1 is dedicated to heating a sample of a coal or a caking additive while maintaining the sample and a material having through-holes from top to bottom surfaces in a constant volume. The apparatus illustrated in FIG. 2 is dedicated to heating a sample of a coal or a caking additive while applying a constant load onto the sample and a through-hole material. A coal or a caking additive is packed at a lower part of a vessel 3 to give a sample 1. A through-hole material 2 is arranged on top of the sample 1. The sample 1 is heated to or above a range of temperatures at which the sample becomes softened and molten, so as to cause the sample to permeate into the through-hole material 2. This permeation distance is measured. The above heating is performed in an inert gas atmosphere. Here, the term "inert gas" refers to a gas that does not react with coal in the measurement temperature range. The typical gases include argon gas, helium gas and nitrogen gas.

In the case where the sample 1 is heated while maintaining the sample 1 and the through-hole material 2 in a constant volume, the pressure during the permeation of the sample can be measured via the through-hole material 2. As illustrated in FIG. 1, a pressure detection rod 4 is arranged on the upper surface of the through-hole material 2, and a load cell 6 is placed in contact with the upper end of the pressure detection rod 4 to measure the pressure. In order to maintain a constant volume, the load cell 6 is fixed so as not to move in a vertical direction. Before starting heating, the through-hole material 2, the pressure detection rod 4 and the load cell 6 are brought into close contact with respect to the sample packed in the vessel 3 so as to make sure that there are no gaps between any of these members. In the case where the through-hole material 2 is a particle-packed layer, the pressure detection rod 4 can be buried into the particle-packed layer. Thus, it is desirable that a plate be inserted between the through-hole material 2 and the pressure detection rod 4.

When the sample 1 is heated while applying a constant load onto the sample 1 and the through-hole material 2, the sample 1 is allowed to be swollen or contracted so as to move the through-hole material 2 in a vertical direction. Thus, the swelling coefficient during sample permeation can be measured via the through-hole material 2. For this purpose, as illustrated in FIG. 2, a swelling coefficient detection rod 13 may be arranged on the upper surface of the through-hole material 2, a loading weight 14 may be placed onto the upper end of the swelling coefficient detection rod 13, and a displacement meter 15 may be arranged above the unit to measure the swelling coefficient. The displacement meter 15 may be one capable of measuring the swelling coefficient in a range in which the sample can be swollen (−100% to 300%). Because the inside of the heating system needs to be maintained in an inert gas atmosphere, a non-contact type displacement meter is suitable, and an optical displacement meter is desirably used. The inert gas atmosphere is preferably a nitrogen atmosphere. In the case where the through-hole material 2 is a particle-packed layer, the swelling coefficient detection rod 13 can be buried into the particle-packed layer. Thus, it is desirable that a plate be inserted between the through-hole material 2 and the swelling coefficient detection rod 13. The load is preferably applied uniformly onto the upper surface of the through-hole material arranged on the upper surface of the sample. It is desired that a pressure of 5 to 80 kPa, preferably 15 to 55 kPa, and most preferably 25 to 50 kPa be applied onto the area of the upper surface of the through-hole material. This pressure is preferably set based on the swelling pressure of a thermally plastic layer in a coke oven. The present inventors studied the reproducibility of measurement results and the power for the detection of brand differences with respect to various kinds of coals. As a result, the present inventors have found that a pressure that is slightly higher than the swelling pressure in an oven, in detail a pressure of about 25 to 50 kPa is most preferable as a measurement condition.

Desirably, the heating means is of a type capable of heating the sample at a predetermined temperature increase rate while measuring the temperature of the sample. Specific examples include an electric furnace, an external heating system that is a combination of a conductive vessel and high-frequency induction, and an internal heating system such as microwaves. In the case where an internal heating system is adopted, a design needs to be devised which allows the inside temperature of the sample to become uniform. For example, it is preferable to design a remedy which increases thermal insulation properties of the vessel.

In order to simulate thermally plastic behaviors of coals and caking additives in a coke oven, the heating rate needs to correspond to a heating rate for the coal in a coke oven. The heating rate for coal around the softening and melting temperatures in a coke oven is generally 2 to 10° C./min, although variable depending on a location inside the oven and operation conditions, and is desirably 2 to 4° C./min, and most desirably about 3° C./min in terms of average heating rate. In the case of low-fluidity coals such as non-coking coals and slightly coking coals, however, heating at 3° C./min results in a small permeation distance and small swelling which can be difficult to detect. It is generally known that coal is improved in fluidity according to a Gieseler plastometer by being rapidly heated (see, for example, Non Patent Literature 3). Thus, in the case of a coal with a permeation distance of, for example, 1 mm or less, the measurement may be performed at an increased heating rate of 10 to 1000° C./min in order to enhance detection sensitivity.

Since the measurement is aimed at evaluating thermal plasticity of coals and caking additives, heating may be performed to such an extent that the temperature is increased to softening and melting temperatures of coals and caking additives. In view of the softening and melting temperatures of coals and caking additives for coke production, heating may be performed at a predetermined heating rate from 0° C. (room temperature) to 550° C., and preferably from 300 to 550° C. that is a range of temperatures at which coal becomes softened and molten.

Figure 3:
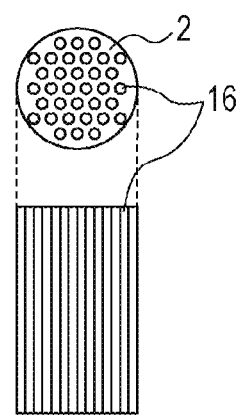
FIG. 3 is a schematic view illustrating a through-hole material with circular through-holes as an example of the through-hole materials for use in the invention.
Figure 4:
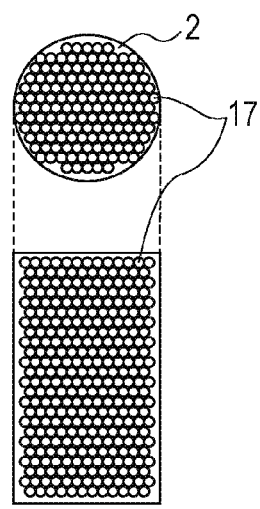
FIG. 4 is a schematic view illustrating a spherical particle-packed layer as an example of the through-hole materials for use in the invention.
Figure 5:
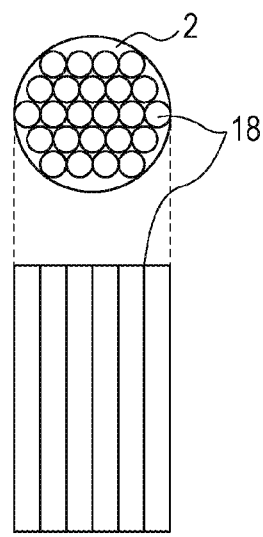
FIG. 5 is a schematic view illustrating a cylinder-packed layer as an example of the through-hole materials for use in the invention.

The through-hole material is desirably one whose permeability coefficient can be measured or calculated beforehand. Exemplary configurations of the materials include integral materials having through-holes, and particle-packed layers. Examples of the integral materials having through-holes include materials having circular through-holes 16 as illustrated in FIG. 3, materials having rectangular through-holes, and materials having irregular through-holes. The particle-packed layers are largely classified into spherical particle-packed layers and non-spherical particle-packed layers. Examples of the spherical particle-packed layers include layers formed of packed particles 17 such as beads as illustrated in FIG. 4. Examples of the non-spherical particle-packed layers include layers of irregular particles and layers formed of packed cylinders 18 as illustrated in FIG. 5. In order to ensure the reproducibility of the measurement, the permeability coefficient is desirably as uniform as possible throughout the material. For simple measurement, it is desired that the material permit easy calculation of its permeability coefficient. Thus, a spherical particle-packed layer is particularly desired for use as the through-hole material in the present invention. The substance which forms the through-hole material is not particularly specified as long as it is not substantially deformed at or above the softening and melting temperatures of coal, in detail until 600° C., and does not react with coal. The height of the material is not particularly limited as long as the material is high enough to accept the permeation of coal melt. In the case where a coal layer with a thickness of 5 to 20 mm is heated, the height of the through-hole material is appropriately about 20 to 100 mm.

It is necessary that the permeability coefficient of the through-hole material be set by assuming the permeability coefficient of large defects present in a coke layer. The present inventors studied a particularly preferred permeability coefficient in the invention while considering constituent factors of such large defects and assuming the sizes thereof. As a result, the present inventors have found that a permeability coefficient of $1 \times 10^8$ to $2 \times 10^9$ m$^{-2}$ is most suitable. This permeability coefficient is derived based on the Darcy's law represented by Equation (1) below:

$$\Delta P/L = K \cdot \mu \cdot u \quad (1)$$

wherein $\Delta P$ is the pressure loss [Pa] inside the through-hole material, L is the height [m] of the through-hole material, K is the permeability coefficient [m$^{-2}$], $\mu$ is the viscosity [Pa·s] of the fluid, and u is the velocity [m/s] of the fluid. For example, in the case where a layer of glass beads with a uniform particle diameter is used as the through-hole material, it is desired to select glass beads with a diameter of about 0.2 mm to 3.5 mm, most desirably 2 mm, in order to achieve the aforementioned suitable permeability coefficient.

Coals and caking additives for measurement samples are crushed beforehand and are packed with a predetermined packing density and a predetermined layer thickness. The crushed particle size may be similar to a particle size of coal charged into a coke oven (particles with a particle diameter of not more than 3 mm representing about 70 to 80 mass % relative to the total). Alternatively, the sample material is preferably crushed such that particles with a particle diameter of not more than 3 mm represent not less than 70 mass %. In view of the fact that the measurement is made with a small apparatus, it is particularly preferable that the whole of the crushed material has a particle diameter of not more than 2 mm. The crushed material may be packed with a density of 0.7 to 0.9 g/cm$^3$ in accordance with a possible packing density in a coke oven. Based on the results of studies on reproducibility and detection power, the present inventors have found that a packing density of 0.8 g/cm$^3$ is preferable. Based on the thickness of a thermally plastic layer in a coke oven, the thickness of the packed layer may be 5 to 20 mm. Studies on reproducibility and detection power made by the present inventors have revealed that a layer thickness of 10 mm is preferable.

It is essentially desired that the permeation distance of a thermally plastic coal or a thermally plastic caking additive be measurable constantly and continuously during heating. However, constant measurement is difficult because of, for example, the influences of tar generated from the sample. Swelling and permeation of coal by heating are irreversible phenomena. Thus, once coal has been swollen or permeated, the shape thereof is substantially maintained even if the coal is cooled. Based on this fact, the measurement may be performed in such a manner that after the permeation of a coal melt has terminated, the entirety of the vessel is cooled and the extent to which the permeation has occurred during heating is determined by measuring the permeation distance after cooling. For example, the through-hole material may be removed from the cooled vessel and the distance may be directly measured with a vernier caliper or a ruler. In the case where the through-hole material is particles, the thermal plastic that has permeated into interparticle voids bonds the particle layer over the distance of permeation. Thus, provided that a relationship between the mass and the height of the particle-packed layer has been measured beforehand, the permeation distance may be calculated by measuring the mass of particles that are not bonded together after the completion of the permeation, and subtracting the measured mass from the initial mass to give the mass of the bonded particles.

Equation (1) described above includes the term of viscosity ($\mu$). Thus, the term of viscosity of the thermal plastic that has permeated into the through-hole material can be derived from the parameters measured according to the invention. For example, in the case where the sample is heated while the sample and the through-hole material are maintained in a constant volume, $\Delta P$ corresponds to the pressure during permeation, L to the permeation distance and u to the permeation velocity, whereby the viscosity term can be derived by substituting the above parameters into Equation (1). Alternatively, in the case where the sample is heated while a constant load is applied onto the sample and the through-hole material, $\Delta P$ corresponds to the pressure of the applied load, L to the permeation distance and u to the permeation velocity, whereby the viscosity can be similarly derived by substituting the above parameters into Equation (1).

As demonstrated above, thermal plasticity of coals and caking additives are evaluated by measuring the permeation distance, the pressure or the swelling coefficient of thermally plastic coals and thermally plastic caking additives. Here, the phrase "thermal plasticity of a sample (a coal or a caking additive) are evaluated" in the invention means that at least the permeation distance, the pressure and the swelling coefficient are measured and, based on the measured values, indicators for quantitatively evaluating behaviors of coal melt as well as consequent phenomena (for example, properties of produced coke, pushing resistance of coke) are obtained. The measured values of the permeation distance, the pressure and the swelling coefficient may be used in combination with other property values (for example, MF). Alternatively, one or more selected from the permeation distance, the pressure and the swelling coefficient alone may be used. In the latter case, the evaluation of thermal plasticity is regarded as being made when the measured values of the permeation distance, the pressure and the swelling coefficient are obtained. That is, measuring the permeation distance, the pressure and the swelling coefficient has substantially the same meaning as evaluating thermal plasticity. Further, the permeation distance, the pressure and the swelling coefficient may be used as parameters in the estimation of coke strength, whereby it becomes possible to manufacture coke having desired strength by blending coals of a number of brands. The most common indicator of coke strength is drum strength at normal temperature. In addition to drum strength, other coke properties such as CSR (coke strength after reaction) (strength after $CO_2$ reaction), tensile strength and microstrength may be estimated based on the above parameters, whereby it becomes possible to produce coke having desired strength by blending coals of a number of brands.

In a conventional coal blending theory for estimating coke strength, coke strength is thought to be determined mainly by an mean maximum vitrinite reflectance (Ro) and a logarithmic value of Gieseler maximum fluidity (MF) (log MF) of coal (see, for example, Non Patent Literature 4). Gieseler fluidity is an indicator of fluidity exhibited when the coal is thermally plastic, and is represented in terms of the rotational speed of a stirring rod of a Gieseler plastometer, namely, the degree of rotations per 1 minute in ddpm (dial division per minute) unit. The coal property used is maximum fluidity (MF). Alternatively, common logarithm of ddpm is sometimes used. Because the permeation distance according to the invention is thought to be a parameter that indicates fluidity under conditions simulating thermally plastic behaviors in a coke oven, this parameter will be superior to a logarithmic value of Gieseler maximum fluidity log MF in estimating coke properties or coke cake structures.

This superiority of the permeation distance is expectable in principle based on the fact that the measurement method simulates an environment in a coke oven, and has been confirmed by the results of a study that examined the influences of the permeation distance on coke strength. In fact, it has been found by the inventive evaluation method that coals with similar log MF have different permeation distances depending on brands. It has been further confirmed that coke strength is affected differently when coals having different permeation distances are blended and produced into coke. In detail, as will be demonstrated in EXAMPLES later, a relation is such that coke strength is decreased after the value of permeation distance exceeds a certain threshold. The reasons for this are considered as follows.

When coals having a long permeation distance are blended, the proportion of coals that exhibit sufficient melting properties during carbonization is considered to be high. It is, however, assumed that coals having an excessively long permeation distance permeate between surrounding coal particles to such a marked extent that regions where these coal particles have been present are left as large cavities, leading to defects. Although a conventional concept based on Gieseler maximum fluidity has anticipated the possibility of a decrease in coke strength in the case of a coal blend exhibiting too high fluidity (see, for example, Non Patent Literature 4), it has yet been impossible to clarify behaviors of individual brands having high fluidity. One of the reasons for this is probably because the conventional Gieseler fluidity measurement is incapable of an accurate measurement of properties at high fluidity due to the aforementioned Weissenberg effect. The inventive measurement method has enabled more accurate evaluation of properties of melts, particularly at high fluidity. Thus, the present invention has made significant advances by making it possible to clarify differences in properties between thermal plastics that have been difficult to distinguish by conventional methods, as well as by allowing for better evaluation of a relationship between thermally plastic behaviors and coke structures.

The present inventors have established suitable measurement conditions in the inventive method, and have completed a method for producing high-strength coke using the measurement results.

EXAMPLES

Example 1

There will be described measurement examples of constant-volume heating for samples of coals and caking additives in combination with a material having through-holes from top to bottom surfaces. The permeation distance and the pressure during permeation were measured using 17 types of coals and 4 types of caking additives (coals A to Q, caking additives R to U) as samples. Table 1 describes properties (mean maximum reflectance: Ro, logarithmic value of Gieseler maximum fluidity: log MF, volatile matter content: VM, ash content: Ash) of the coals and the caking additives used. The measurement of the fluidity of the caking additives used herein by a Gieseler plastometer method resulted in common logarithmic values of all of these Gieseler maximum fluidities (log MF) being 4.8, which was the detection limit.

TABLE 1

| Coal | Ro [%] | log MF [log ddpm] | VM [mass %] | Ash [mass %] |
|---|---|---|---|---|
| Coal A | 0.66 | 3.55 | 43.2 | 5.8 |
| Coal B | 0.67 | 1.00 | 36.6 | 9.0 |
| Coal C | 0.72 | 3.61 | 40.8 | 9.0 |
| Coal D | 0.73 | 2.29 | 36.2 | 8.8 |
| Coal E | 0.75 | 2.32 | 38.1 | 9.7 |
| Coal F | 0.79 | 3.96 | 37.2 | 7.9 |
| Coal G | 0.91 | 3.59 | 33.0 | 7.9 |
| Coal H | 0.99 | 2.84 | 29.1 | 8.6 |
| Coal I | 1.00 | 1.71 | 25.8 | 9.6 |
| Coal J | 1.00 | 2.20 | 27.7 | 10.4 |
| Coal K | 1.03 | 2.97 | 28.2 | 9.6 |
| Coal L | 1.30 | 1.34 | 21.0 | 9.4 |
| Coal M | 1.31 | 1.26 | 20.4 | 7.3 |
| Coal N | 1.38 | 2.49 | 20.9 | 10.9 |
| Coal O | 1.44 | 2.03 | 21.1 | 9.3 |
| Coal P | 1.54 | 0.00 | 16.6 | 8.3 |
| Coal Q | 1.62 | 0.70 | 18.8 | 9.6 |
| Caking additive R | — | Not less than 4.8 | — | Less than 1 |
| Caking additive S | — | Not less than 4.8 | — | Less than 1 |
| Caking additive T | — | Not less than 4.8 | — | Less than 1 |
| Caking additive U | — | Not less than 4.8 | — | Less than 1 |

With use of an apparatus similar to that illustrated in FIG. 1, the permeation distance and the pressure during permeation were measured. The heating system was a high-frequency induction heating system. That is, a heating element 8 and a vessel 3 in FIG. 1 were an induction heating coil and a dielectric graphite vessel. The vessel 3 was 18 mm in diameter and 37 mm in height. Glass beads having a diameter of 2 mm were used as a through-hole material 2. The vessel was charged with 2.04 g of a sample that had been crushed to a particle diameter of not more than 2 mm and had been vacuum dried at room temperature. A weight weighing 200 g was dropped from above the sample five times with a fall distance of 20 mm, thereby packing the sample. (At this time, the thickness of the sample layer was 10 mm.) Next, the glass beads with a 2 mm diameter were arranged on the packed layer of the sample 1 so as to achieve a thickness of 25 mm, thereby preparing a glass bead-packed layer as the through-hole material 2. On the glass bead-packed layer, a sillimanite disk with a diameter of 17 mm and a thickness of 5 mm was arranged, and a quartz rod as a pressure detection rod 4 was further arranged thereon. With use of nitrogen gas as an inert gas, the sample was heated from room temperature to 550° C. at a heating rate of 3° C./min. During the heating, the pressure transmitted via the pressure detection rod 4 was measured with a load cell 6. After the completion of the heating, cooling was performed in a nitrogen atmosphere. The beads that had not adhered to the thermal plastic were collected from the cooled vessel 3, and the mass thereof was measured.

The permeation distance was determined on the basis of the packing height of the bead layer that had adhered together. A relationship had been obtained beforehand between the packing height and the mass of the glass bead-packed layer, whereby it became possible that from the mass of beads adhering together with the thermal plastic, the packing height of such glass beads was derived as shown in Equation (2) below. The permeation distance was derived from Equation (2).

$$L = (G-M) \times H \qquad (2)$$

wherein L is the permeation distance [mm], G the mass [g] of the packed glass beads, M the mass [g] of the beads that had not adhered together with the thermal plastic, and H the height of the packed layer per 1 g of the glass beads packed into this experimental apparatus [mm/g].

For the caking additives, the permeation distance was measured by using a sample vessel with the same diameter as described above but with a height of 100 mm, and by arranging a glass bead-packed layer with a thickness of 80 mm onto the sample. This configuration was adopted because the permeation distance of caking additives was large. Separately, tests were carried out in which a coal was packed with a constant sample layer thickness while changing the height of the vessel and the thickness of the glass bead-packed layer. The measured values of the permeation distance were identical as long as the thickness of the glass bead-packed layer was greater than the permeation distance.

Figure 6:
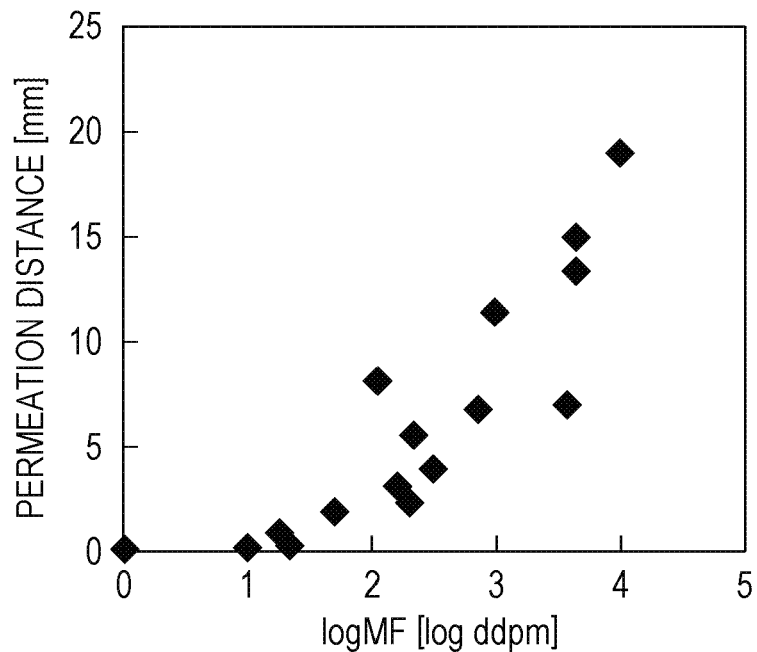
FIG. 6 is a graph showing results of the measurement of the permeation distance of thermally plastic coals in EXAMPLE 1.

Table 2 describes the measurement results of the permeation distance and the maximum pressure during permeation. FIG. 6 shows a relationship between the measurement results of the permeation distance and the logarithmic values of Gieseler maximum fluidity (log MF). (Plotting excluded values of caking additives whose MF value was not measured accurately.)

TABLE 2

| Coal | Permeation distance [mm] | Maximum pressure [kPa] |
|---|---|---|
| Coal A | 6.9 | 25 |
| Coal B | 0.2 | 16 |
| Coal C | 13.3 | 15 |
| Coal D | 2.4 | 6 |
| Coal E | 5.5 | 25 |
| Coal F | 19.0 | 18 |
| Coal G | 14.9 | 23 |
| Coal H | 6.8 | 7 |
| Coal I | 1.9 | 10 |
| Coal J | 3.2 | 16 |
| Coal K | 11.5 | 21 |
| Coal L | 0.3 | 5 |
| Coal M | 0.9 | 0 |
| Coal N | 4.0 | 20 |
| Coal O | 8.1 | 68 |
| Coal P | 0.0 | 0 |
| Coal Q | 0.8 | 6 |
| Caking additive R | 58.0 | 2 |
| Caking additive S | 48.0 | 2 |
| Caking additive T | 50.0 | 4 |
| Caking additive U | 65.0 | 1 |

From FIG. 6, the permeation distance showed a certain extent of correlation with log MF, though a number of brands deviated from the correlation. Further, the measurement results for the caking additives in Table 2 have shown that the differences in properties of caking additives were successfully observed. Such discrimination has been impossible with conventional methods. In a measurement in which a sample and a through-hole material are heated in a constant volume, the factors that will affect the permeation distance are, as shown in Equation (1), the viscosity $\mu$ of the sample and the swelling pressure $\Delta P$ of the sample, which vary from sample to sample. Thus, the permeation distances and the pressures measured while heating the samples of coals and caking additives in combination with the through-hole material in a constant volume are considered to reflect the state of the melt in a coke oven. Because the melt condition and the pressure of thermally plastic coals and thermally plastic caking additives are assumed to affect the structure of coke after carbonization, it can be said that such parameters are particularly effective in the estimation of coke strength.

Further, because the pressure exerted during the permeation of the sample is the result of pressure measurement carried out in a measurement environment simulating swelling behaviors in a coke oven, it can be said that this parameter is effectively used in order to estimate the pressure applied to the wall of a coke oven during the carbonization of coal in a coke oven.

Example 2

Measurement examples will be described in which coals and caking additives as samples were heated while applying a constant load to the sample and a material having through-holes from top to bottom surfaces. The permeation distance and the swelling coefficient during permeation were measured with respect to the same coals and caking additives as in EXAMPLE 1, namely, 17 types of coals and 4 types of caking additives (coals A to Q, caking additives R to U) shown in Table 1. With use of an apparatus similar to that illustrated in FIG. 2, the permeation distance and the swelling coefficient during permeation were measured. The heating system was a high-frequency induction heating system. That is, a heating element 8 and a vessel 3 in FIG. 2 were an induction heating coil and a dielectric graphite vessel. The vessel 3 was 18 mm in diameter and 37 mm in height. Glass beads having a diameter of 2 mm were used as a through-hole material. The vessel 3 was charged with 2.04 g of a sample that had been crushed to a particle diameter of not more than 2 mm and had been vacuum dried at room temperature. A weight weighing 200 g was dropped from above the sample five times with a fall distance of 20 mm, thereby packing the sample 1. Next, the glass beads with a 2 mm diameter were arranged on the packed layer of the sample 1 so as to achieve a thickness of 25 mm, thereby preparing a glass bead-packed layer as the through-hole material 2. On the glass bead-packed layer, a sillimanite disk with a diameter of 17 mm and a thickness of 5 mm was arranged, and a quartz rod as a swelling coefficient detection rod 13 was further arranged thereon. Furthermore, a weight 14 weighing 1.3 kg was placed on top of the quartz rod. As a result, the pressure applied onto the sillimanite disk was 50 kPa. With use of nitrogen gas as an inert gas, the sample was heated to 550° C. at a heating rate of 3° C./min. During the heating, a displacement was measured with a laser displacement meter, and the swelling coefficient was calculated from the height with which the sample had been packed. After the completion of the heating, cooling was performed in a nitrogen atmosphere. The beads that had not adhered to the thermal plastic were collected from the cooled vessel, and the mass thereof was measured. The permeation distance was derived from Equation (2).

In the measurement of the permeation distance of the caking additives in this example too, tests were carried out while using a larger vessel and increasing the thickness of the glass bead-packed layer similarly in EXAMPLE 1. It was confirmed that the thickness of the glass bead-packed layer did not affect the measured values of the permeation distance under the conditions of EXAMPLE 2.

Figure 7:
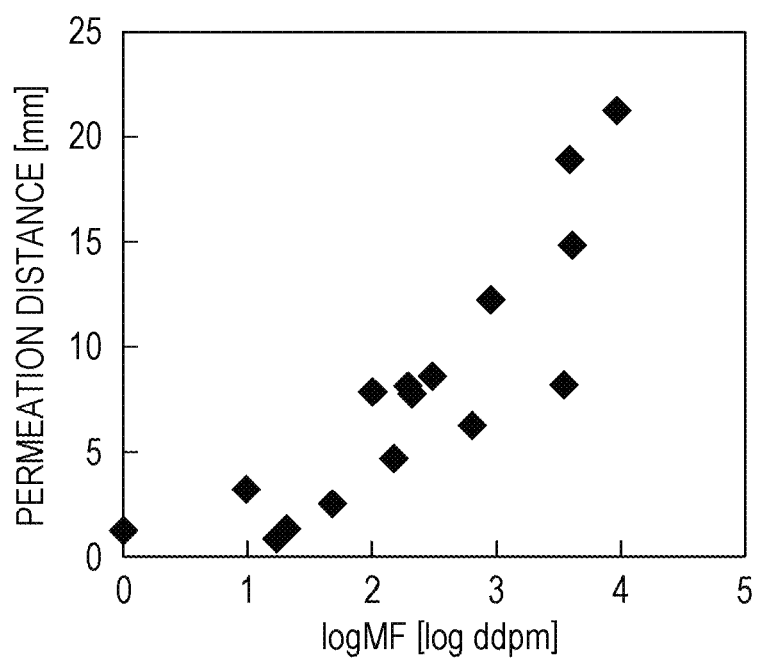
FIG. 7 is a graph showing results of the measurement of the permeation distance of thermally plastic coals in EXAMPLE 2.

Table 3 describes the measurement results of the permeation distance and the final swelling coefficient. FIG. 7 shows a relationship between the measurement results of the permeation distance and the logarithmic values of Gieseler maximum fluidity (log MF). (Plotting excluded values of caking additives whose MF value was not measured accurately.)

TABLE 3

| Coal | Permeation distance [mm] | Final swelling coefficient [%] |
|---|---|---|
| Coal A | 8.2 | −9 |
| Coal B | 3.3 | −9 |
| Coal C | 14.9 | −41 |
| Coal D | 8.1 | −8 |
| Coal E | 8.0 | −9 |
| Coal F | 21.3 | −55 |
| Coal G | 19.0 | −48 |
| Coal H | 6.3 | −9 |
| Coal I | 2.5 | −16 |
| Coal J | 4.8 | −16 |
| Coal K | 12.1 | −16 |
| Coal L | 1.3 | −2 |
| Coal M | 0.9 | −9 |
| Coal N | 8.7 | −15 |
| Coal O | 7.8 | 4 |
| Coal P | 1.2 | 0 |
| Coal Q | 3.0 | 11 |
| Caking additive R | 65.0 | −82 |
| Caking additive S | 52.0 | −75 |
| Caking additive T | 55.0 | −81 |
| Caking additive U | 70.0 | −85 |

From FIG. 7, the permeation distance measured in this example is shown to have a certain extent of correlation with log MF. However, it is also found that some brands exhibited different permeation distances even though their log MF values were similar. In particular, this tendency was seen in a higher log MF region. In view of the fact that the error of the measurement of the permeation distance with this apparatus was found to be 0.6 in terms of standard error by repeating a test three times under the same conditions, a significant difference in permeation distance was shown with respect to the coal H and the coal K having substantially equal log MF. Based on only the relation represented by Equation (1), it can be assumed that brands with the same log MF will have a similar viscosity $\mu$ in a molten state, and thus the permeation distances will be identical. The reasons for this assumption are because $\Delta P$ and K are constant in this measurement irrespective of the samples to be analyzed, as well as because log MF of a coal is substantially correlated with temperatures at which the coal exhibits melting properties (herein, such temperatures correspond to melting time), and therefore the term u can be regarded to be substantially constant. During carbonization of coal, however, gas generation and swelling phenomena are observed simultaneously with melting of the coal due to driving off of volatile matters. Thus, the values of the permeation distance obtained in this measurement are assumed to reflect the combined influences of the permeation of the melt into the bead-packed layer and the gas generation from the melt in the bead layer. Because these values are assumed to be factors that determine the structure of coke after carbonization, it can be said that such parameters are particularly effective in the estimation of coke strength.

Further, the final swelling coefficients described in Table 3 are swelling coefficient values at 550° C. Because the results in Table 3 come from the measurement of swelling coefficient in a measurement environment simulating swelling behaviors in a coke oven, it can be said that the data are effective for estimating coke strength as well as for estimating a gap between the wall of a coke oven and a mass of coke.

Example 3

Whether there was an additivity of the permeation distance was investigated according to the same measurement method as in EXAMPLE 2.

Figure 8:
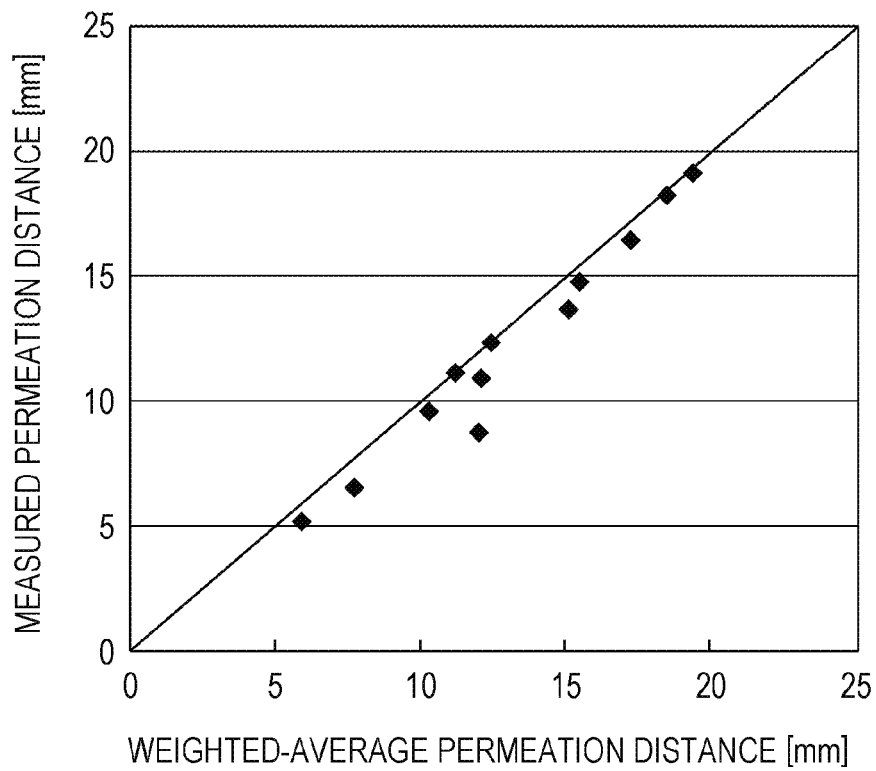
FIG. 8 is a graph showing a relationship between the measured permeation distance and the weighted-average permeation distance of thermally plastic coal blends in EXAMPLE 3.

Two brands were selected from 4 types of coals (coals V to Y) and were blended at various blend ratios to give coal blends as samples. The samples were subjected to the measurement of the permeation distance. Table 4 describes the coals used and properties (Ro, log MF, VM, Ash) of the coal blends. Here, the properties of the coal blends are weighted-average values of properties of individual coals averaged according to the blending proportions. The measurement results of the permeation distance are also described in Table 4. FIG. 8 shows a relationship between the weighted-average permeation distances and the measured permeation distances of the coal blends.

estimating the permeation distance by calculating the weighted-average value.

With regard to coals used for coal blends, various qualities and grades are usually measured beforehand with respect to each brand, and the obtained data are used in the blending of coals. Accordingly, it is practically preferable that the permeation distance be measured beforehand with respect to each lot of brand, thereby enabling smooth calculation of the permeation distance of a coal blend.

Example 4

The values of thermal plasticity of coals obtained in the present invention were applied to the estimation of coke strength and the effectiveness thereof was examined.

As described above, the permeation distance according to the invention is considered to be a parameter superior to a logarithmic value of Gieseler maximum fluidity log MF in the estimation of coke properties and coke cake structures. Thus, a carbonization test and a test of coke strength after carbonization were carried out as outlined below in order to examine how coke strength would be affected when coke were produced using coals having substantially the same log MF and different permeation distances.

Referring to Table 1 used in EXAMPLES 1 and 2, the coal A, the coal F and the coal G (each with log MF of not less than 3.5) were selected as "similar MF coals". Each of these coals was blended at 20 mass % together with various coals as the

TABLE 4

| Coal | Blend ratio (%) | | | | Ro [%] | logMF [log ddpm] | VM [%] | Ash [%] | Permeation distance [mm] |
| --- | --- | --- | --- | --- | --- | --- | --- | --- | --- |
| | Coal V | Coal W | Coal X | Coal Y | | | | | |
| Coal V | 100 | 0 | 0 | 0 | 0.80 | 4.00 | 35.9 | 8.9 | 21.5 |
| Coal W | 0 | 100 | 0 | 0 | 1.00 | 3.08 | 27.7 | 10.4 | 12.9 |
| Coal X | 0 | 0 | 100 | 0 | 0.72 | 2.40 | 35.9 | 9.1 | 9.4 |
| Coal Y | 0 | 0 | 0 | 100 | 1.29 | 0.48 | 20.8 | 7.6 | 2.5 |
| Coal blend VW1 | 75 | 25 | 0 | 0 | 0.85 | 3.77 | 33.9 | 9.3 | 19.1 |
| Coal blend VW2 | 50 | 50 | 0 | 0 | 0.90 | 3.54 | 31.8 | 9.7 | 16.4 |
| Coal blend VW3 | 25 | 75 | 0 | 0 | 0.95 | 3.31 | 29.8 | 10.0 | 13.6 |
| Coal blend VX1 | 75 | 0 | 25 | 0 | 0.78 | 3.60 | 35.9 | 9.0 | 18.2 |
| Coal blend VX2 | 50 | 0 | 50 | 0 | 0.76 | 3.20 | 35.9 | 9.0 | 14.8 |
| Coal blend VX3 | 25 | 0 | 75 | 0 | 0.74 | 2.80 | 35.9 | 9.1 | 12.3 |
| Coal blend VY1 | 50 | 0 | 0 | 50 | 1.05 | 2.24 | 28.4 | 8.3 | 8.7 |
| Coal blend WX1 | 0 | 75 | 25 | 0 | 0.93 | 2.91 | 29.8 | 10.1 | 10.9 |
| Coal blend WX2 | 0 | 50 | 50 | 0 | 0.86 | 2.74 | 31.8 | 9.8 | 11.1 |
| Coal blend WX3 | 0 | 25 | 75 | 0 | 0.79 | 2.57 | 33.9 | 9.4 | 9.5 |
| Coal blend WY1 | 0 | 50 | 0 | 50 | 1.15 | 1.78 | 24.3 | 9.0 | 6.5 |
| Coal blend XY1 | 0 | 0 | 50 | 50 | 1.01 | 1.44 | 28.4 | 8.4 | 5.2 |

From FIG. 8, it has been shown that there is a very good additivity for the permeation distances measured in this example. Accordingly, the permeation distance value of a coal blend formed of two or more types of coals may be determined by actually measuring the permeation distance of a sample of the coal blend, or by previously measuring the permeation distances of individual coals to be blended and balance such that the weighted-average Ro values and the weighted-average log MF values of the coal blends as a whole would be the same, thereby preparing coal blends (coal blends A, F and G). The coal A, the coal F and the coal G are such types of coals which have a high MF among coals used in coke producing and are frequently used in order to improve the adhesiveness of coal particles in coke producing. Further, coal blends including a number of brands with log MF≥3.0 at the same time (coal blend AF, coal blend FG and coal blend FGK) were prepared in order to test properties of coal blends containing such high-MF coals. These coal blends were prepared such that the average qualities and grades would be Ro=0.99 to 1.05 and log MF=2.0 to 2.3. Table 5 describes the brands and the proportions of the coals used in the respective coal blends, the weighted-average constant-volume permeation distances (calculated from the values in Table 2) and the weighted-average constant-pressure permeation distances (calculated from the values in Table 3) of the coals with log MF≥3.0 in the coal blends, and the strength of the produced coke.

in each coal blend with a logarithmic value of Gieseler maximum fluidity of log MF≥3.0 (the permeation distance measured in EXAMPLE 2 by heating the coal sample while applying a constant load onto the coal sample and the through-hole material), and the drum strength of the carbonized coke from each coal blend. From the comparison of the strengths of the coal blend A, the coal blend F and the coal blend G which contained the coal A, the coal F and the coal G, respectively, at 20 mass % as the similar MF coal, the drum strength was shown to be higher as the permeation distance of the similar MF coal was shorter. Further, the results of the drum strengths of the coal blend A, the coal blend F and the coal blend AF show that there is an additivity between the

TABLE 5

| Coal | Coal blend A [mass %] | Coal blend F [mass %] | Coal blend G [mass %] | Coal blend AF [mass %] | Coal blend FG [mass %] | Coal blend FGK [mass %] |
|---|---|---|---|---|---|---|
| Coal A | 20 | 0 | 0 | 10 | 0 | 0 |
| Coal B | 11 | 12 | 19 | 11 | 0 | 0 |
| Coal D | 0 | 0 | 0 | 0 | 17 | 20 |
| Coal F | 0 | 20 | 0 | 10 | 11 | 11 |
| Coal G | 0 | 0 | 20 | 0 | 17 | 14 |
| Coal H | 18 | 20 | 3 | 20 | 20 | 0 |
| Coal I | 19 | 20 | 18 | 20 | 0 | 0 |
| Coal J | 8 | 10 | 20 | 9 | 0 | 0 |
| Coal K | 0 | 0 | 0 | 0 | 0 | 20 |
| Coal L | 0 | 0 | 0 | 0 | 22 | 23 |
| Coal M | 9 | 6 | 9 | 7 | 0 | 0 |
| Coal N | 10 | 8 | 6 | 8 | 0 | 0 |
| Coal P | 0 | 0 | 0 | 0 | 13 | 12 |
| Coal Q | 5 | 4 | 5 | 5 | 0 | 0 |
| Average volume-constant permeation distance (mm) of coal with logMF ≥ 3.0 | 6.9 | 19.0 | 14.9 | 13.0 | 16.5 | 14.4 |
| Average pressure-constant permeation distance (mm) of coal with logMF ≥ 3.0 | 8.2 | 21.3 | 19.0 | 14.7 | 19.9 | 16.5 |
| Coke strength DI150/15 [—] | 80.9 | 79.6 | 79.4 | 80.3 | 79.9 | 81.2 |
| MSI (+65) [%] | 54.4 | 52.1 | 52.3 | 54.4 | 52.8 | 54.2 |
| CRI [%] | — | — | — | — | 29.7 | 29.5 |
| CSR [%] | — | — | — | — | 55.4 | 59.5 |

Each of the coals in Table 5 was used after being crushed such that particles with a particle diameter of not more than 3 mm represented 100 mass %. Further, the water content was adjusted such that the water content in the whole coal blend would be 8 mass %. The coal blend weighing 16 kg was packed into a carbonization can such that the bulk density would be 750 kg/m$^3$, and a 10 kg weight was placed thereon. The coal blend was then carbonized in an electric furnace at a furnace wall temperature of 1050° C. for 6 hours, removed from the furnace, and cooled in a nitrogen atmosphere to give a coke. The coke strength of the obtained coke was determined based on a drum strength testing method in accordance with JIS K 2151, in which the drum was rotated at 15 rpm and the mass proportion of coke particles that had a particle diameter of not less than 15 mm after 150 rotations was calculated. The mass ratio thereof to the mass proportion before the rotations was calculated to give a drum strength index DI 150/15. Further, the results of measurements of CRI ($CO_2$ reactivity), CSR (strength after $CO_2$ reaction, all measured in accordance with an ISO 18894 method), and microstrength (MSI+65) are also described.

Figure 9:
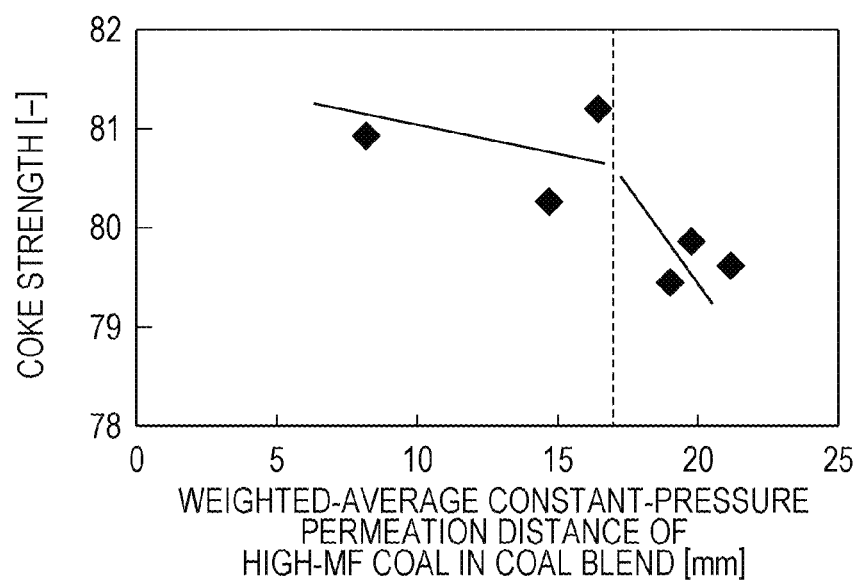
FIG. 9 is a graph showing a relationship between the weighted-average permeation distance (measured by heating under a constant load) of a coal with a logarithmic value of Gieseler maximum fluidity of log MF 3.0 that is added to a coal blend, and the drum strength measured in EXAMPLE 4.

FIG. 9 shows a relationship between the weighted-average value of the constant-pressure permeation distance of the coal permeation distance and the drum strength of the similar MF coals. These results, in combination with the results of the coal blend FG and the coal blend FGK, show that the coke strength decreases when the weighted-average value of the constant-pressure permeation distance of the coal in the coal blend with a logarithmic value of Gieseler maximum fluidity of log MF 3.0 exceeds 17 mm. Thus, the producing of high-strength coke can be realized by regulating the weighted-average value of the constant-pressure permeation distance of the coal in the coal blend with a logarithmic value of Gieseler maximum fluidity of log MF≥3.0 to be not more than 17 mm.

Figure 10:
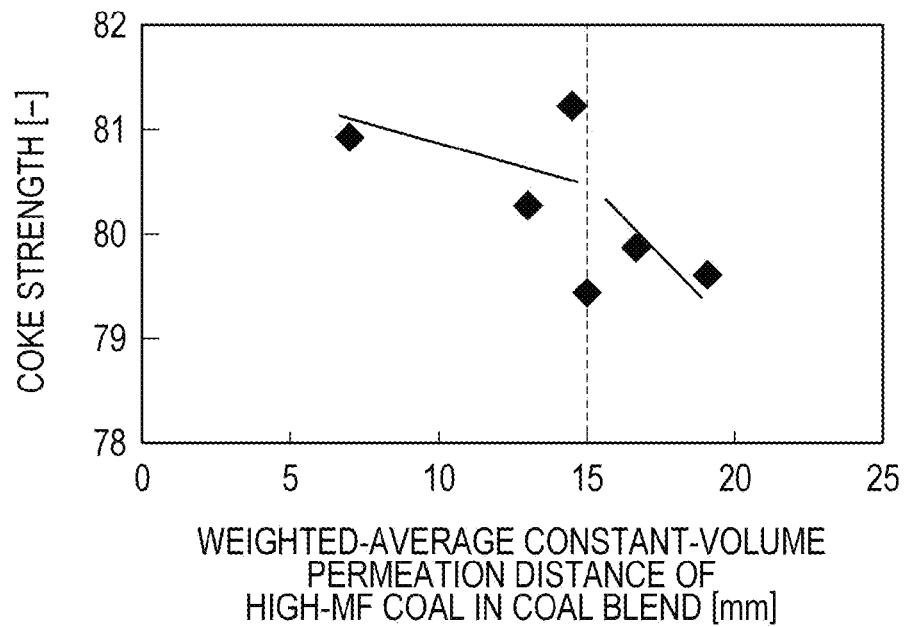
FIG. 10 is a graph showing a relationship between the weighted-average permeation distance (measured by heating in a constant volume) of a coal with a logarithmic value of Gieseler maximum fluidity of log MF 3.0 that is added to a coal blend, and the drum strength measured in EXAMPLE 4.

Next, FIG. 10 shows a relationship between the weighted-average value of the constant-volume permeation distance of the coal in each coal blend with a logarithmic value of Gieseler maximum fluidity of log MF≥3.0 (the permeation distance measured in EXAMPLE 1 by heating the coal sample in combination with the through-hole material in a constant volume), and the drum strength of the carbonized coke from each coal blend.

A similar tendency, although slightly weaker than in FIG. 9, was confirmed also in FIG. 10. Thus, it has been shown that the values of the permeation distance obtained in this measurement affect coke strength in both cases in which such values are determined by the constant-volume heating measurement and by the constant-load heating measurement. It has been determined that when the constant-volume permeation distance is adopted as an indicator, the weighted-average value of the constant-volume permeation distance of the coal in the coal blend with a logarithmic value of Gieseler maximum fluidity of log MF≥3.0 is preferably regulated to be not more than 15 mm. Because the measurement of the permeation distance with respect to an identical coal affords different results depending on the measurement conditions used, it is necessary that coals be each evaluated under substantially identical conditions. Here, the term "substantially identical" means that the products of the sample layer thickness and the packing density are within ±20%, the types of the through-hole materials (for example, spherical particle-packed layers or cylinder-packed layers) are the same but the diameters of the spheres or the cylinders are within ±20%, and the heating rates are within ±20%. The measurement conditions may be used practically without any problems as long as the differences are within the above ranges. By previously obtaining, based on values measured under such conditions as defined above, correlations as illustrated in FIGS. 9 and 10 between the permeation distance of a high-MF coal in a coal blend and the strength of coke obtained by carbonization of the coal blend, it becomes possible to determine the extent to which the permeation distance of the high-MF coal should be adjusted in order to obtain a desired coke strength. Further, CSR was measured with respect to the coke produced from the coal blend FG and the coal blend FGK. As a result, a similar tendency to the JIS drum strength was observed, with CSR of the coke from the coal blend FG being 55.4 (reactivity CRI=29.7) and CSR of the coke from the coal blend FGK being 59.5 (reactivity CRI=29.5). In general, it is known that when the reactivities CRI of coke are similar, CSR shows a good correlation with JIS drum strength. This tendency was confirmed also with the samples in EXAMPLES. Similar tendencies to JIS drum strength were also observed for microstrength and indirect tensile strength.

As demonstrated above, it has been revealed that the permeation distance of a high-MF coal greatly affects coke strength. In particular, the reason why the permeation distance of a high-MF coal has marked effects is probably because differences in permeation distance become larger as coals have higher MF, as shown in FIG. 6 and FIG. 7. Low-MF coals have limited differences in permeation distance among brands, and thus it is probable that their permeation distances did not exert significant influences. Further, it is probable that the evaluation of thermal plasticity of high-MF coals by a Gieseler plastometer method has been insufficient due to the aforementioned Weissenberg effect and the presence of measurable upper limit. The inventive method improves defects possessed by conventional methods, and will make it possible to obtain a new finding concerning the influences of thermal plasticity on coke strength.

Figure 11:
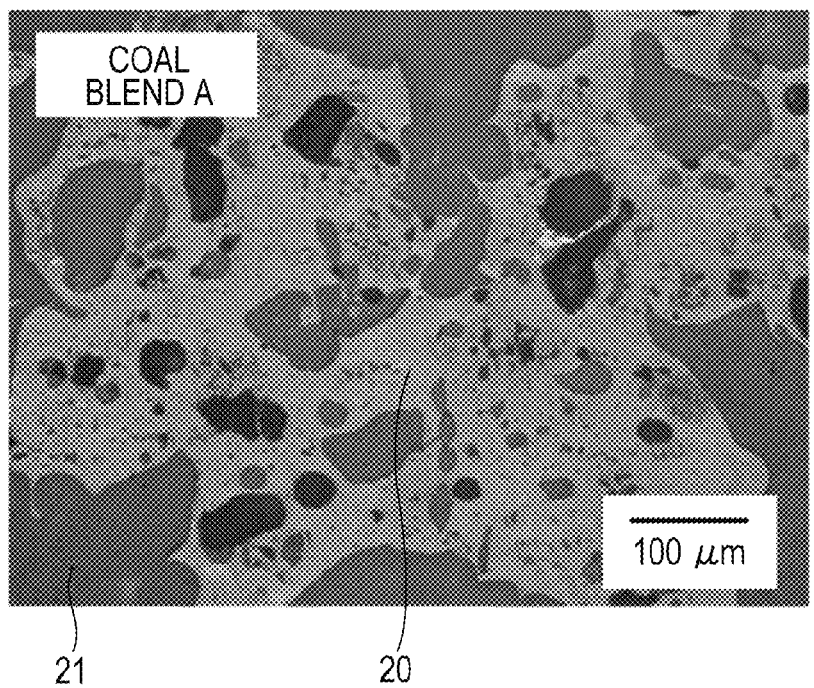
FIG. 11 is a picture showing a structure of coke obtained by carbonization of a coal blend A that contained coal A having a suitable permeation distance.
Figure 12:
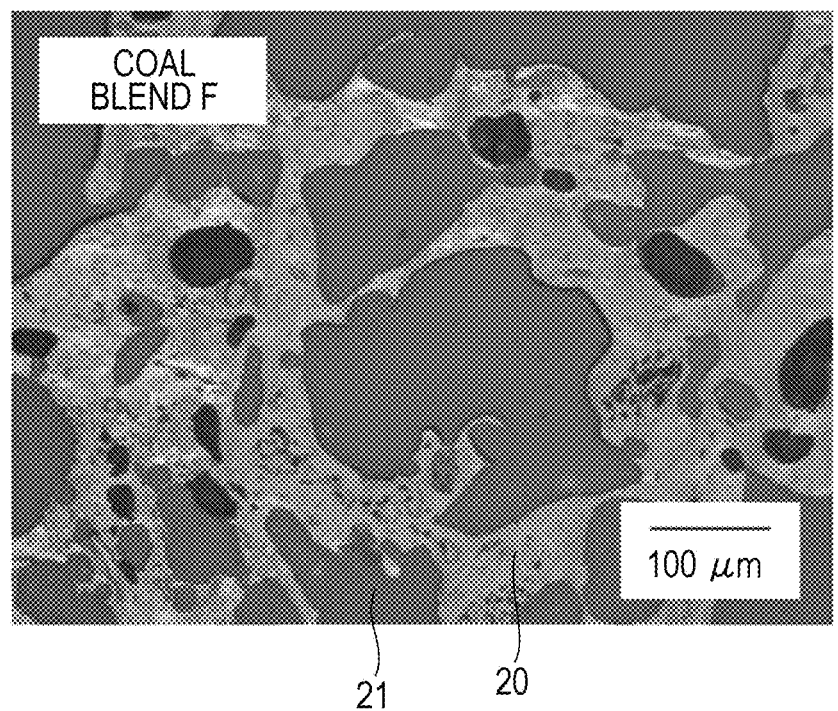
FIG. 12 is a picture showing a structure of coke obtained by carbonization of a coal blend F that contained coal F having an excessively large permeation distance.

Next, the reasons why the permeation distance affected coke strength were examined by observing with an optical microscope the structure of coke obtained by carbonization of the coal blend A which contained 20 mass % of the coal A whose permeation distance was thought to be appropriate, as well as the structure of coke obtained by carbonization of the coal blend F which contained 20 mass % of the coal F whose permeation distance was thought to be excessively long. FIG. 11 and FIG. 12 show pictures of the coal blend A and the coal blend F, respectively, taken at 100× magnification.

From the comparison between the pictures shown in FIG. 11 and FIG. 12, it has been shown that the coke from carbonization of the coal blend F that contained the coal F with an excessively long permeation distance had thinner pore walls 20 and distorted large pores 21 as a result of linking together of pores, compared to the coke from carbonization of the coal blend A that contained the coal A with an appropriate permeation distance. It has been reported that coke strength becomes higher as pore walls are thicker and pores have a higher circularity (see, for example, Non Patent Literature 5). Accordingly, it has been confirmed that the permeation distance of coal affects the formation of a coke structure during carbonization and consequently affects the strength of the coke.

The results in EXAMPLES show that the permeation distance, which is measured by heating the coal sample while applying a constant load onto the coal sample and the through-hole material or by heating the coal sample while maintaining the sample and the through-hole material in a constant volume, is a factor which affects the strength of coke produced from the coal and which cannot be accounted for with conventional factors, as well as show that the utilization of the permeation distance in combination with other conventional parameters in the estimation of coke strength will allow for highly accurate estimation of strength. Further, it is now apparent that the producing of high-strength coke is possible by blending coals based on the permeation distances measured under the preferred conditions.

REFERENCE SIGNS LIST

1 SAMPLE
2 THROUGH-HOLE MATERIAL HAVING THROUGH-HOLES FROM TOP TO BOTTOM SURFACES
3 VESSEL
4 PRESSURE DETECTION ROD
5 SLEEVE
6 LOAD CELL
7 THERMOMETER
8 HEATING ELEMENT
9 TEMPERATURE DETECTOR
10 TEMPERATURE CONTROLLER
11 GAS INLET
12 GAS OUTLET
13 SWELLING COEFFICIENT DETECTION ROD
14 WEIGHT
15 DISPLACEMENT METER
16 CIRCULAR THROUGH-HOLE
17 PACKED PARTICLE
18 PACKED CYLINDER
20 PORE WALL
21 PORE

The invention claimed is:

1. A method for evaluating thermal plasticity of coals and caking additives, comprising:
    packing a coal or a caking additive into a vessel to prepare a sample,
    arranging a through-hole material having through-holes from top to bottom surfaces, onto the sample,
    heating the sample while maintaining the sample and the through-hole material in a constant volume,
    measuring the permeation distance with which the molten sample has permeated into the through-holes, and
    evaluating thermal plasticity of the sample using the measured value.

2. A method for evaluating thermal plasticity of coals and caking additives, comprising:
    packing a coal or a caking additive into a vessel to prepare a sample, arranging a through-hole material having through-holes from top to bottom surfaces, onto the sample, heating the sample while maintaining the sample and the through-hole material in a constant volume, measuring the pressure of the sample that is transmitted via the through-hole material, and evaluating thermal plasticity of the sample using the measured value.

3. A method for evaluating thermal plasticity of coals and caking additives, comprising:

packing a coal or a caking additive into a vessel to prepare a sample, arranging a through-hole material having through-holes from top to bottom surfaces, onto the sample, heating the sample while applying a constant load onto the through-hole material, measuring the permeation distance with which the molten sample has permeated into the through-holes, and evaluating thermal plasticity of the sample using the measured value.

4. A method for evaluating thermal plasticity of coals and caking additives, comprising:

packing a coal or a caking additive into a vessel to prepare a sample, arranging a through-hole material having through-holes from top to bottom surfaces, onto the sample, heating the sample while applying a constant load onto the through-hole material, measuring the swelling coefficient of the sample, and evaluating thermal plasticity of the sample using the measured value.

5. The method for evaluating thermal plasticity of coals and caking additives described in claim 1, wherein the preparation of the sample includes crushing a coal or a caking additive such that particles with a particle diameter of not more than 3 mm account for not less than 70 mass %, and packing the crushed coal or caking additive into a vessel with a packing density of 0.7 to 0.9 g/cm$^3$ and a layer thickness of 5 to 20 mm.

6. The method for evaluating thermal plasticity of coals and caking additives described in claim 5, wherein the coal or the caking additive is crushed such that particles with a particle diameter of not more than 2 mm account for 100 mass %.

7. The method for evaluating thermal plasticity of coals and caking additives described in claim 1, wherein the through-hole material is a spherical particle-packed layer or a non-spherical particle-packed layer.

8. The method for evaluating thermal plasticity of coals and caking additives described in claim 7, wherein the through-hole material is a spherical particle-packed layer.

9. The method for evaluating thermal plasticity of coals and caking additives described in claim 8, wherein the spherical particle-packed layer include glass beads.

10. The method for evaluating thermal plasticity of coals and caking additives described in claim 1, wherein the sample is heated from room temperature to 550° C. at a heating rate of 2 to 10° C./min in an inert gas atmosphere.

11. The method for evaluating thermal plasticity of coals and caking additives described in claim 10, wherein the heating rate is 2 to 4° C./min.

12. The method for evaluating thermal plasticity of coals and caking additives described in claim 3, wherein the application of a constant load includes applying such a load that the pressure to the top surface of the through-hole material becomes 5 to 80 kPa.

13. The method for evaluating thermal plasticity of coals and caking additives described in claim 12, wherein the application of a load includes applying such a load that the pressure to the top surface of the through-hole material becomes 15 to 55 kPa.

14. The method for evaluating thermal plasticity of coals and caking additives described in claim 1, wherein arranging of the through-hole material includes arranging glass beads having a diameter of 0.2 to 3.5 mm onto the sample so as to obtain a layer thickness of 20 to 100 mm, and heating of the sample includes heating the sample from room temperature to 550° C. at a heating rate of 2 to 10° C./min in an inert gas atmosphere while maintaining the sample and the glass bead layer in a constant volume.

15. The method for evaluating thermal plasticity of coals and caking additives described in claim 3, wherein arranging of the through-hole material includes arranging glass beads having a diameter of 0.2 to 3.5 mm onto the sample so as to obtain a layer thickness of 20 to 100 mm, and heating of the sample includes heating the sample from room temperature to 550° C. at a heating rate of 2 to 10° C./min in an inert gas atmosphere while applying a load from above the glass beads such that 5 to 80 kPa is obtained.

16. The method for evaluating thermal plasticity of coals and caking additives described in claim 1, wherein the preparation of the sample includes crushing a coal or a caking additive such that particles with a particle diameter of not more than 3 mm account for not less than 70 mass %, and packing the crushed coal or caking additive into a vessel with a packing density of 0.7 to 0.9 g/cm$^3$ and a layer thickness of 5 to 20 mm, arranging of the through-hole material includes arranging glass beads having a diameter of 0.2 to 3.5 mm onto the sample so as to obtain a layer thickness of 20 to 100 mm, and heating of the sample includes heating the sample from room temperature to 550° C. at a heating rate of 2 to 10° C./min in an inert gas atmosphere while maintaining the sample and the glass bead layer in a constant volume.

17. The method for evaluating thermal plasticity of coals and caking additives described in claim 3, wherein the preparation of the sample includes crushing a coal or a caking additive such that particles with a particle diameter of not more than 3 mm account for not less than 70 mass %, and packing the crushed coal or caking additive into a vessel with a packing density of 0.7 to 0.9 g/cm$^3$ and a layer thickness of 5 to 20 mm, arranging of the through-hole material includes arranging glass beads having a diameter of 0.2 to 3.5 mm onto the sample so as to obtain a layer thickness of 20 to 100 mm, and heating of the sample includes heating the sample from room temperature to 550° C. at a heating rate of 2 to 10° C./min in an inert gas atmosphere while applying a load from above the glass beads such that 5 to 80 kPa is obtained.

18. The method for evaluating thermal plasticity of coals and caking additives described in claim 1, wherein the preparation of the sample includes crushing a coal or a caking additive such that particles with a particle diameter of not more than 2 mm account for 100 mass %, and packing the crushed coal or caking additive into a vessel with a packing density of 0.8 g/cm$^3$ and a layer thickness of 10 mm, arranging of the through-hole material includes arranging glass beads having a diameter of 2 mm onto the sample so as to obtain a layer thickness of 80 mm, and heating of the sample includes heating the sample from room temperature to 550° C. at a heating rate of 3° C./min in an inert gas atmosphere while maintaining the sample and the glass bead layer in a constant volume.

19. The method for evaluating thermal plasticity of coals and caking additives described in claim 3, wherein the preparation of the sample includes crushing a coal or a caking additive such that particles with a particle diameter of not more than 2 mm account for 100 mass %, and packing the crushed coal or caking additive into a vessel with a packing density of 0.8 g/cm³ and a layer thickness of 10 mm, arranging of the through-hole material includes arranging glass beads having a diameter of 2 mm onto the sample so as to obtain a layer thickness of 80 mm, and heating of the sample includes heating the sample from room temperature to 550° C. at a heating rate of 3° C./min in an inert gas atmosphere while applying a load from above the glass beads such that 50 kPa is obtained.

20. A method for producing coke, comprising:

measuring the permeation distance, which is a thermal plasticity of coal, with respect to a coal or coals to be added to a coking coal blend that have a logarithmic value of Gieseler maximum fluidity, log MF, of not less than 3.0;

wherein the step of measuring the permeation distance includes, packing the coal or coals to be added into a vessel to prepare a sample, arranging a through-hole material having through-holes from top to bottom surfaces, onto the sample, heating the sample while maintaining the sample and the through-hole material in a constant volume or while applying a constant load onto the through-hole material, and measuring the permeation distance with which the molten sample has permeated into the through-holes;

based on a weighted-average value of the measured permeation distance(s), determining the blend ratio of the coal(s) having a logarithmic value of Gieseler maximum fluidity, log MF, of not less than 3.0; and carbonizing coals that have been blended according to the determined blend ratio.

21. The method for producing coke described in claim 20, wherein the permeation distance is measured by (1) to (4) below, and the blend ratio is determined by determining the proportion(s) of the coal(s) having a logarithmic value of Gieseler maximum fluidity, log MF, of not less than 3.0 such that the weighted-average value of the measured permeation distance(s) becomes not more than 15 mm, (1) the coal or coals to be added is crushed such that particles with a particle diameter of not more than 2 mm account for 100 mass %, and the crushed coal or caking additive is packed into the vessel with a packing density of 0.8 g/cm³ and a layer thickness of 10 mm, thereby preparing the sample, (2) the through-hole material is glass beads having a diameter of 2 mm that are arranged onto the sample so as to obtain a layer thickness of 80 mm, (3) the sample is heated from room temperature to 550° C. at a heating rate of 3° C./min in an inert gas atmosphere while maintaining the sample and the glass bead layer in a constant volume, (4) the permeation distance of the molten sample that has permeated into the glass bead layer is measured.

22. The method for producing coke described in claim 20, wherein the permeation distance is measured by (1) to (4) below, and the blend ratio is determined by determining the proportion(s) of the coal(s) having a logarithmic value of Gieseler maximum fluidity, log MF, of not less than 3.0 such that the weighted-average value of the measured permeation distance(s) becomes not more than 17 mm, (1) the coal or coals to be added is crushed such that particles with a particle diameter of not more than 2 mm account for 100 mass %, and the crushed coal or caking additive is packed into the vessel with a packing density of 0.8 g/cm³ and a layer thickness of 10 mm, thereby preparing the sample, (2) the through-hole material is glass beads having a diameter of 2 mm that are arranged onto the sample so as to obtain a layer thickness of 80 mm, (3) the sample is heated from room temperature to 550° C. at a heating rate of 3° C./min in an inert gas atmosphere while applying a load from above the glass beads such that 50 kPa is obtained, (4) the permeation distance of the molten sample that has permeated into the glass bead layer is measured.

23. A method for producing coke, comprising:

determining beforehand brands of coals or caking additives to be added to a coking coal blend, as well as the total blend ratio of a coal or coals with log MF of less than 3.0 relative to the coal blend, measuring the permeation distance with respect to a coal or coals having a logarithmic value of Gieseler maximum fluidity, log MF, of not less than 3.0, among the coals to be added to the coking coal blend;

wherein the step of measuring the permeation distance includes, packing the coal or coals to be added into a vessel to prepare a sample, arranging a through-hole material having through-holes from top to bottom surfaces, onto the sample, heating the sample while maintaining the sample and the through-hole material in a constant volume or while applying a constant load onto the through-hole material, and measuring the permeation distance with which the molten sample has permeated into the through-holes;

determining a relationship between the weighted-average permeation distance of the coals or caking additives with log MF of not less than 3.0 that are to be added to the coal blends, and the coke strength obtained with the coal blends prepared while changing the proportions of the individual brands of coals, the relationship being obtained by changing the proportions of the individual brands of coals or caking additives with the total blend ratio of the coal or coals with log MF of less than 3.0 being kept constant relative to the coal blend; and adjusting the weighted-average permeation distance by controlling the brand and the proportion of the coal(s) with log MF of not less than 3.0 so as to achieve coke strength that is not less than a desired value.

24. The method for producing coke described in claim 23, wherein the permeation distance is measured under conditions selected from the range described below:

- the coal or coals to be added is crushed such that particles with a particle diameter of not more than 3 mm account for not less than 70 mass %;
- the crushed material is packed into the vessel with a packing density of 0.7 to 0.9 g/cm$^3$ and a layer thickness of 5 to 20 mm, thereby preparing the sample;
- the through-hole material is glass beads having a diameter of 0.2 to 3.5 mm that are arranged onto the sample so as to obtain a layer thickness of 20 to 100 mm; and
- the sample is heated from room temperature to 550° C. at a temperature increase rate of 2 to 10° C./min in an inert gas atmosphere while maintaining the sample and the glass bead layer in a constant volume.

25. The method for producing coke described in claim 23, wherein the permeation distance is measured under conditions selected from the range described below:

- the coal or coals to be added is crushed such that particles with a particle diameter of not more than 3 mm account for not less than 70 mass %;
- the crushed material is packed into the vessel with a packing density of 0.7 to 0.9 g/cm$^3$ and a layer thickness of 5 to 20 mm, thereby preparing the sample;
- the through-hole material is glass beads having a diameter of 0.2 to 3.5 mm that are arranged onto the sample so as to obtain a layer thickness of 20 to 100 mm; and
- the sample is heated from room temperature to 550° C. at a temperature increase rate of 2 to 10° C./min in an inert gas atmosphere while applying a load from above the glass beads such that a pressure of 5 to 80 kPa is obtained.

* * * * *